United States Patent [19]

Nadelson

[11] 4,131,679

[45] * Dec. 26, 1978

[54] SUBSTITUTED 4-HYDROXY PYRIDONES

[75] Inventor: Jeffrey Nadelson, Denville, N.J.

[73] Assignee: Sandoz, Inc., E. Hanover, N.J.

[*] Notice: The portion of the term of this patent subsequent to May 17, 1994, has been disclaimed.

[21] Appl. No.: 819,006

[22] Filed: Jul. 26, 1977

[51] Int. Cl.² .................... A61K 31/44; C07D 211/74
[52] U.S. Cl. .................................... 424/263; 546/296; 546/116
[58] Field of Search ........... 260/296 H, 296 R, 297 Z; 424/263

[56] References Cited

U.S. PATENT DOCUMENTS

| | | | |
|---|---|---|---|
| 4,024,262 | 5/1977 | Nadelson | 424/263 |
| 4,049,813 | 9/1977 | Nadelson | 260/296 H |
| 4,064,251 | 12/1977 | Nadelson | 424/263 |

OTHER PUBLICATIONS

Burger, Medicinal Chemistry, 2nd ed., pp. 79 and 81, Interscience Publishers, Inc. NY (1960).

Primary Examiner—John D. Randolph
Attorney, Agent, or Firm—Gerald D. Sharkin; Robert S. Honor; Timothy G. Rothwell

[57] ABSTRACT

This disclosure describes novel compounds of the formula:

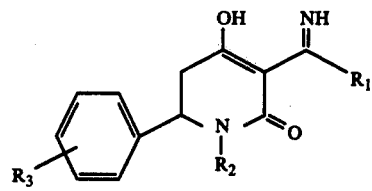

where
$R_1$ is straight chain lower alkyl or

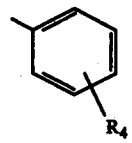

where
$R_4$ is hydrogen or halo having an atomic weight of about 19 to 36, and
$R_2$ is straight chain lower alkyl, and
$R_3$ is hydrogen or halo as defined above, which are useful as minor tranquilizers and muscle relaxants.

7 Claims, No Drawings

SUBSTITUTED 4-HYDROXY PYRIDONES

This invention relates to substituted 4-hydroxy pyridones which exhibit minor tranquilizer and muscle relaxant acitivity. In particular, it relates to 3-substituted-5,6-dihydro-4-hydroxy-1-methyl-6-subsituted or unsubstituted phenyl-2(1H)-pyridone, intermediates thereof, and pharmaceutically acceptable salts.

The compound of this invention may be represented by the following structural formula:

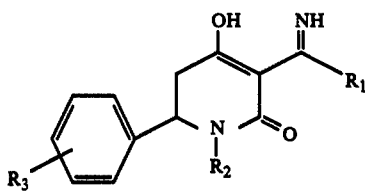

where
 $R_1$ is straight chain lower alkyl, i.e., straight chain lower alkyl having 1 to 4 carbon atoms, e.g., methyl, ethyl, propyl and the like, or

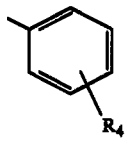

where
 $R_4$ is hydrogen or halo having an atomic weight of about 19 to 36, and
 $R_2$ is straight chain lower lower alkyl as defined above, and
 $R_3$ is hydrogen or halo as defined above.

The compounds of formula (I) are prepared according to the following reaction scheme:

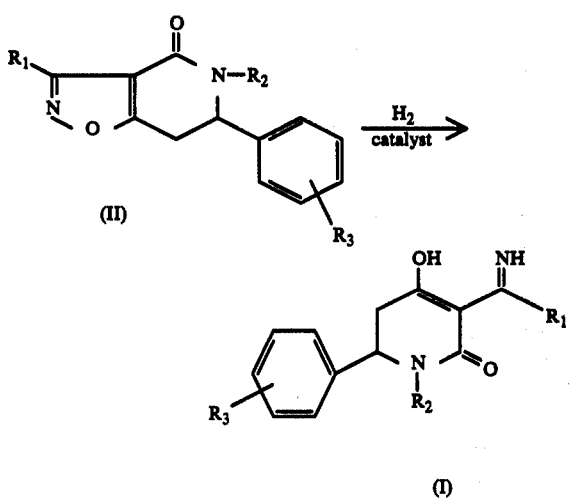

where $R_1$, $R_2$ and $R_3$ are as defined above.

The compounds of formula (I) are prepared by reducing a compound of the formula (II) under hydrogen gas in the presence of a catalyst and an inert organic solvent. Although the particular catalyst employed is not critical, the preferred catalysts include palladium on carbon, platinum oxide, raney nickel and the like, preferably palladium on carbon. The particular solvent is not critical, but it is preferred that the reaction be run in the presence of the lower alkanols, e.g., methanol, ethanol, and the like, preferably ethanol. The temperature of the reaction is not critical, but it is preferred that the reaction be run from about 10° to 50° C., preferably from about 20° to 30° C. The reaction is run from about 1 to 10 hours, preferably from about 2 to 3 hours. The product is recovered using conventional techniques, e.g., filtration.

The compounds of formula (II) are prepared according to the following reaction scheme:

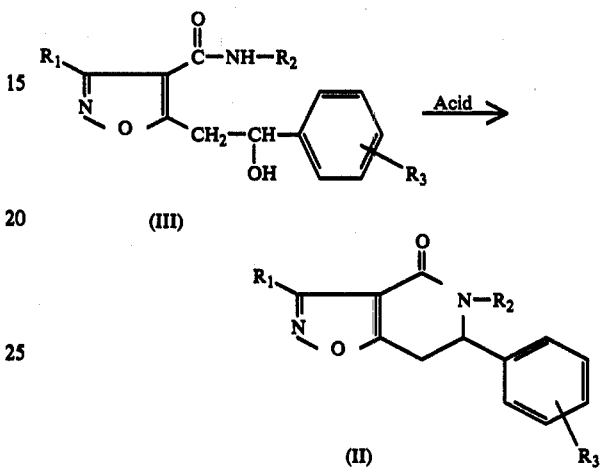

where $R_1$, $R_2$ and $R_3$ are as defined above.

The compounds of formula (II) are prepared by treating a compound of the formula (III) with polyphosphoric acid in the presence of an inert solvent. Although the particular solvent employed is not critical, the preferred solvents include the aromatic hydrocarbons such as benzene, toluene and the like, or an excess of the acid utilized above, the latter being especially preferred. The temperature of the reaction is not critical, but it is preferred that the reaction be run from about 80° to 120° C., preferably from about 100° to 105° C. The reaction is run from about 2 to 8 hours, preferably from about 4 to 6 hours. The product is recovered using conventional techniques, e.g., filtration followed by recrystallization.

The compounds of formula (III) are prepared according to the following reaction scheme:

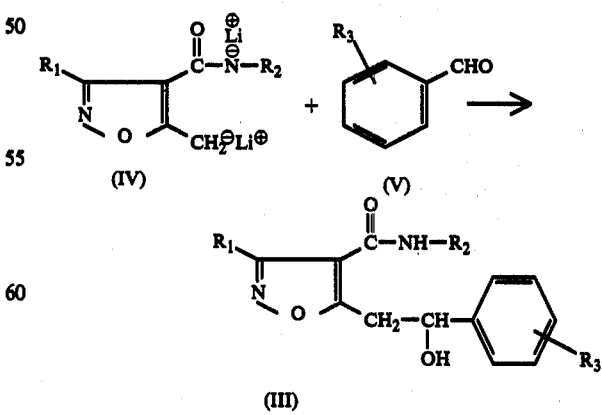

where $R_1$, $R_2$ and $R_3$ are as defined above.

The compounds of formula (III) are prepared by treating a compound of the formula (IV) with a compound of the formula (V) in the presence of an inert organic solvent. Although the particular solvent employed is not critical, the preferred solvents include an ether such as diethylether or tetrahydrofuran or an aliphatic hydrocarbon such as pentane, hexane, heptane and the like, preferably tetrahydrofuran. The temperature of the reaction is not critical, but it is preferred that the reaction be run at a temperature of from about $-75°$ to $-55°$ C., preferably from about $-65°$ to $-60°$ C. The reaction is run from about 1 to 5 hours, preferably from about 2.5 to 3.5 hours. The product is recovered using conventional techniques, e.g., trituration followed by filtration.

The compounds of formula (IV) may be prepared according to the following reaction scheme:

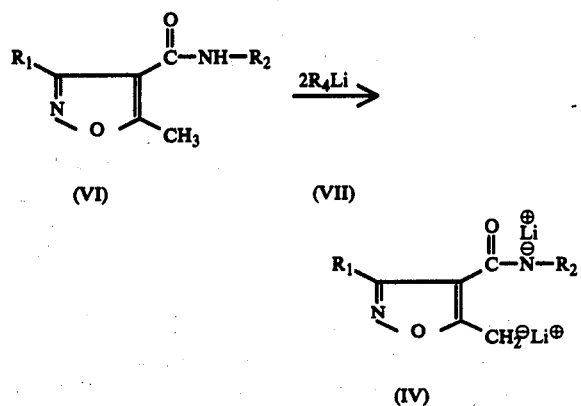

where $R_4$ is lower alkyl having 1 to 4 carbon atoms, and $R_1$ and $R_2$ are as defined above.

The compounds of formula (IV) are prepared by treating a compound of the formula (VI) with a compound of the formula (VII) in the presence of an inert organic solvent. Although the particular solvent employed is not critical, the preferred solvients include an ether such as diethylether or tetrahydrofuran or an aliphatic hydrocarbon such as pentane, hexane, heptane and the like, preferably hexane. The temperature of the reaction is not critical, but it is preferred that the reaction be run at a temperature of from about $-75°$ to $-55°$ C., preferably from about $-65°$ to $-60°$ C. The reaction is run from about 1 to 5 hours, preferably from about 2.5 to 3.5 hours. The product of the compound of formula (IV) is not isolated but employed in situ as a starting material in the preparation of the compounds of formula (III).

The compound of formula (I) may exist in the following tautomeric forms, and these tautomeric forms are also included within the scope of this invention:

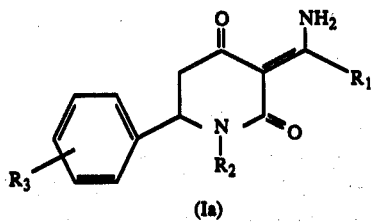

where $R_1$, $R_2$ and $R_3$ are as defined above.

Many of the compounds of formulae (III), (IV), (V), (VI) and (VII) are known and may be prepared by methods described in the literature. The compounds of formulae (III), (IV), (V), (VI) and (VII) not specifically described may be prepared by analogous methods from known starting materials.

The compounds of formula (I) are useful because they possess pharmacological activity in animals as muscle relaxants and minor tranquilizers as indicated (1) by the hexobarbital reinduction method of Winter, J. Pharmacol. and Exp. Therap., 91, 7-11, 1948; (2) by their ability to produce docility in behavior tests in mice given 45 to 150 mg/kg of animal body weight, i.p. of the test compound according to the 30-word adjective check sheet system basically as described by Irwin S. (Gordon Research Conference, Medicinal Chemistry, 1959) and Chen (Symposium on Sedative and Hypnotic Drugs, Williams and Wilkins, 1954); (3) by their ability to antagonize chlonic convulsions and death in mice given about 35 mg/kg of the test compound followed immediately by 30 to 250 mg/kg i.p. of N-sulfamoylazepine; (4) by scoring for loss of righting reflex according to the method of Reed-Muench (American Journal of Hygiene, 27: 493-497, 1938), in which mice are administered 12.5 mg/kg, i.p. Thioridazine, immediately after which the test compound is administered at dosages of 30 to 100 mg/kg in a volume of 0.1 ml/10 g. body weight. Sixty minutes after dosing, the mice are scored for loss of righting refex and (5) by their activity in the rotorod test as described by Dunham and Miya (J. Am. Pharm. Assoc., 45: 208, 157).

For such usage, the compounds (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups, and elixirs and parenterally as solutions, suspensions, dispersions, emulsions and the like, e.g., a sterile injectable aqueous solution. The dosage will vary depending upon the mode of administration utilized and the particular compound employed.

For minor tranquilizer use in the treatment of anxiety and tension, the effective dosage will vary depending on the particular compound employed. However, in general, satisfactory results are obtained when the compounds are administered orally at a daily dosage of from about 10.0 milligrams to about 200 milligrams per kilogram of animal body weight, typically given in divided doses two to four times per day. For most large mammals, the total daily dosage is from about 50 to about 500 milligrams, and dosage forms suitable for internal administration comprise from about 12.5 to about 250 milligrams of the compound in admixture with a solid or liquid pharmaceutical carrier or diluent.

For muscle relaxant use in the treatment of muscle spasms, the effective dosage will vary depending on the particular compound employed. However, in general, satisfactory results are obtained when the compuounds are administered orally at a daily dosage of from about 10.0 milligrams to about 200 milligrams per kilogram of animal body weight typically given in divided doses two to four times per day. For most large mammals, the total daily dosage is from about 50 to about 500 milligrams and dosage forms suitable for internal administration comprise from about 12.5 to about 250 milligrams of the compound in admixture with a solid or liquid pharmaceutical carrier or diluent.

The compounds of formula (I) may be similarly administered in the form of their non-toxic pharmaceutically acceptable salts. Such salts possess the same order of activity as the free acid and are readily prepared by reacting the compound with a pharmaceutically acceptable base by conventional techniques and, accordingly, are included within the scope of this invention. Representative of such salts are the alkali metal salts, e.g., salts with lithium, sodium, potassium and the like, and the alkali earth metal salts such as salts with magnesium, calcium and the like.

Tablets and capsules containing the ingredients indicated below may be prepared by conventional techniques and are useful as minor tranquilizers and muscle relaxants in divided doses two to four times per day.

| Ingredients | Weight (mg.) tablet | capsule |
| --- | --- | --- |
| 3-α-iminobenzyl-5,6-dihydro-4-hydroxy-1-methyl-6-phenyl-2(1H)-pyridone | 200 | 200 |
| tragacanth | 10 | — |
| lactose | 247.5 | 300 |
| corn starch | 25 | — |
| talcum | 15 | — |
| magnesium stearate | 2.5 | — |
| TOTAL | 500 mg. | 500 mg. |

EXAMPLE 1

3-Phenyl-5-(β-hydroxyphenethyl)-N-methyl-isoxazole-4-carboxamide.

A suspension of 75 g. (0.348 mole) of 3-phenyl-5,N-dimethyl-isoxazole-4-carboxamide and 1 liter of tetrahydrofuran is cooled to −65° C. and 478 ml. of 1.6M n-butyllithium in hexane (0.765 mole) is added dropwise maintaining the temperature between −60° and −70° C. After the addition is complete, the orange suspension is stirred for 1½ hours at −60° to −70° C., and then 37.2 g. (0.350 mole) of benzaldehyde in 375 ml. tetrahydrofuran is added dropwise maintaining the temperature between −60° and −70° C. After addition is complete the mixture is stirred 1½ hours at −60° to −70° C. and then warmed to −30° C. and quenched by the addition of saturated ammonium chloride solution. The mixture is further diluted with tetrahydrofuran and the layers are separated. The tetrahydrofuran layer is washed twice with 50% brine, and once with brine, dried over anhydrous magnesium sulfate, filtered with a 50:50 mixture of ether:petroleum ether, filtered and washed with cold ether to give 3-phenyl-5-(β-hydroxyphenethyl)-N-methyl-isoxazole-4-carboxamide; m.p. 183°–184° C.

Following the above procedure and using in place of 3-phenyl-N-methyl-isoxazole-4-carboxamide, an equivalent amount of (a) 3-(p-chlorophenyl)-5,N-dimethyl-isoxazole-4-carboxamide,
(b) 3-(p-fluorophenyl)-5,N-dimethyl-isoxazole-4-carboxamide,
(c) 3-(o-fluorophenyl)-5,N-dimethyl-isoxazole-4-carboxamide, or
(d) 3-ethyl-5,N-dimethyl-isoxazole-4-carboxamide, there is obtained
(a) 3-(p-chlorophenyl)-5-(β-hydroxyphenethyl)-N-methyl-isoxazole-4-carboxamide,
(b) 3-(p-fluorophenyl)-5-(β-hydroxyphenethyl)-N-methyl-isoxazole-4-carboxamide,
(c) 3-(o-fluorophenyl)-5-(β-hydroxyphenethyl)-N-methyl-isoxazole-4-carboxamide, or
(d) 3-ethyl-5-(β-hydroxyphenethyl)-N-methyl-isoxazole-4-carboxamide, respectively.

Again following the same procedure and using in place of benzaldehyde and equivalent amount of (e) p-chlorobenzaldehyde,
(f) p-fluorobenzaldehyde, or
(g) o-fluorobenzaldehyde, there is obtained
(e) 3-phenyl-5-(4-chloro-β-hydroxyphenethyl)-N-methyl-isoxazole-4-carboxamide,
(f) 3-phenyl-5-(4-fluoro-β-hydroxyphenethyl)-N-methyl-isoxazole-4-carboxamide, or
(g) 3-phenyl-5-(2-fluoro-β-hydroxyphenethyl)-N-methyl-isoxazole-4-carboxamide, respectively.

Also following the above procedure and using in place of 3-phenyl-5,N-dimethyl-isoxazole-4-carboxamide an equivalent amount of (h) 3-(p-fluorophenyl)-5,N-dimethyl-isoxazole-4-carboxamide,
(i) 3-(o-fluoropheny)-5,N-dimethyl-isoxazole-4-carboxamide, and in place of benzaldehyde an equivalent amount of
(h) p-fluorobenzaldehyde,
(i) o-fluorobenzaldehyde there is obtained
(h) 3-(p-fluorophenyl)-5-(4-fluoro-β-hydroxyphenethyl)-N-methyl-isoxazole-carboxamide, or
(i) 3-(o-fluorophenyl)-5-(2-fluoro-β-hydroxyphenethyl)-N-methyl-isoxazole-carboxamide, respectively.

EXAMPLE 2

5-Methyl-6,7-dihydro-3,6-diphenyl-isoxazole[4,5-c]pyridin-4(5H)-one.

To 550 ml. of polyphosphoric acid maintained at a temperature of 100° to 105° C. there is added 36.5 grams (0.114 moles) 3-phenyl-5-(β-hydroxyphenethyl)-N-methyl-isoxazole-4-carboxamide in portions. The mixture is then stirred at 100° for 5 hours and then poured onto 2 liters of ice and water. The resulting solid is filtered and purified by recrystallization to give 5-methyl-6,7-dihydro-3,6-diphenyl isoxazolo[4,5-c]pyridin-4-(5H)-one; m.p. 108° to 111° C.

Following the above procedure and using in place of 3-phenyl-5-(β-hydroxyphenethyl)-N-methyl-isoxazole-4-carboxamide, an equivalent amount of (a) 3-(p-chlorophenyl)-5-(β-hydroxyphenethyl)-N-methyl-isoxazole-4-carboxamide,
(b) 3-(p-fluorophenyl)-5-(β-hydroxyphenethyl)-N-methyl-isoxazole-4-carboxamide,
(c) 3-(o-fluorophenyl)-5-(β-hydroxyphenethyl)-N-methyl-isoxazole-4-carboxamide,
(d) 3-ethyl-5-(β-hydroxyphenethyl)-N-methyl-isoxazole-4-carboxamide,
(e) 3-phenyl-5-(4-chloro-β-hydroxyphenethyl)-N-methyl-isoxazole-4-carboxamide, (f) 3-phenyl-5-(4-fluoro-β-hydroxyphenethyl)-N-methyl-isoxazole-4-carboxamide,
(g) 3-phenyl-5-(2-fluoro-β-hydroxyphenethyl)-N-methyl-isoxazolo-4-carboxamide,
(h) 3-(p-fluorophenyl)-5-(4-fluoro-β-hydroxyphenethyl)-N-methyl-isoxazole-4-carboxamide, or
(i) 3-(o-fluorophenyl)-5-(2-fluoro-β-hydroxyphenethyl)-N-methyl-isoxazole-4-carboxamide, there is obtained
(a) 5-methyl-6,7-dihydro-3-(p-chlorophenyl)-6-phenyl-isoxazolo[4,5-c]pyridin-4(5H)-one,
(b) 5-methyl-6,7-dihydro-3-(p-fluorophenyl)-6-phenyl-isoxazolo[4,5-c]pyridin-4(5H)-one,
(c) 5-methyl-6,7-dihydro-3-(o-fluorophenyl)-6-phenyl-isoxazolo[4,5-c]pyridin-4(5H)-one,
(d) 3-ethyl-5-methyl-6,7-dihydro-6-phenyl-isoxazolo[4,5-c]pyridin-4(5H)-one,
(e) 5-methyl-6,7-dihydro-3-phenyl-6-(p-chlorophenyl)-isoxazolo[4,5-c]pyridin-4(5H)-one.
(f) 5-methyl-6,7-dihydro-3-phenyl-6-(p-fluorophenyl)-isoxazolo[4,5-c]pyridin-4(5H)-one,
(g) 5-methyl-6,7-dihydro-3-phenyl-6-(o-fluorophenyl)-isoxazolo[4,5-c]pyridin-4(5H)-one,
(h) 5-methyl-6,7-dihydro-3-(p-fluorophenyl)-6-(p-fluorophenyl)-isoxazolo[4,5-c]pyridin-4(5H)-one, or
(i) 5-methyl-6,7-dihydro-3-(o-fluorophenyl)-6-(o-fluorophenyl)-isoxazolo[4,5-c]pyridin-4(5H)-one, respectively.

EXAMPLE 3

3-α-iminobenzyl-5,6-dihydro-4-hydroxy-1-methyl-6-phenyl-2(1H)-pyridone.

A mixture of 4 grams (0.013 mole) of 5-methyl-6,7-dihydro-3,6-diphenyl isoxazolo[4,5-c]pyridin-4(5H)-one, 0.44 grams palladium on carbon and 80 ml. ethanol is hydrogenated at 50 psi until the equivalent amount of hydrogen is absorbed. The catalyst is filtered and washed thoroughly with ethanol. The ethanol is evaporated in vacuo and the residue recrystallized to give 3-α-iminobenzyl-5,6-dihydro-4-hydroxy-1-methyl-6-phenyl-2(1H)-pyridone; m.p. 117° to 120° C.

Following the above procedure and using in place of 5-methyl-6,7-dihydro-3,6-diphenyl-isoxazolo[4,5-c]pyridin-4(5H)-one an equivalent amount of
(a) 5-methyl-6,7-dihydro-3-(p-chlorophenyl)-6-phenyl-isoxazolo[4,5-c]pyridin-4(5H)-one,
(b) 5-methyl-6,7-dihydro-3-(p-fluorophenyl)-6-phenyl-isoxazolo[4,5-c]pyridin-4(5H)-one,
(c) 5-methyl-6,7-dihydro-3-(o-fluorophenyl)-6-phenyl-isoxazolo[4,5-c]pyridin-4(5H)-one,
(d) 3-ethyl-5-methyl-6,7-dihydro-6-phenyl-isoxazolo[4,5-c]pyridin-4(5H)-one,
(e) 5-methyl-6,7-dihydro-3-phenyl-6-(p-chlorophenyl)-isoxazolo[4,5-c]pyridin-4(5H)-one,
(f) 5-methyl-6,7-dihydro-3-phenyl-6-(p-fluorophenyl)-isoxazolo[4,5-c]pyridin-4(5H)-one,
(g) 5-methyl-6,7-dihydro-3-phenyl-6-(o-fluorophenyl)-isoxazolo[4,5-c]pyridin-4(5H)-one,
(h) 5-methyl-6,7-dihydro-3-(p-fluorophenyl)-6-(p-fluorophenyl)-isoxazolo[4,5-c]pyridin-4(5H)-one, or
(i) 5-methyl-6,7-dihydro-3-(o-fluorophenyl)-6-(o-fluorophenyl)-isoxazolo[4,5-c]pyridin-4(5H)-one, there is obtained
(a) 3-(α-imino-p-chlorobenzyl)-5,6-dihydro-4-hydroxy-6-phenyl-1-methyl-2(1H)-pyridone,
(b) 3-(α-imino-p-fluorobenzyl)-5,6-dihydro-4-hydroxy-6-phenyl-1-methyl-2(1H)-pyridone,
(c) 3-(α-imino-o-fluorobenzyl)-5,6-dihydro-4-hydroxy-6-phenyl-1-methyl-2(1H)-pyridone,
(d) 3-(1-iminopropyl)-5,6-dihydro-4-hydroxy-6-phenyl-1-methyl-2(1H)-pyridone,
(e) 3-(α-iminobenzyl)-5,6-dihydro-4-hydroxy-6-(p-chlorophenyl)-1-methyl-2(1H)-pyridone,
(f) 3-(α-iminobenzyl)-5,6-dihydro-4-hydroxy-6-(p-fluorophenyl)-1-methyl-2-(1-H)-pyridone,
(g) 3-(α-iminobenzyl)-5,6-dihydro-4-hydroxy-6-(o-fluorophenyl)-1-methyl-2(1H)-pyridone,
(h) 3-(α-imino-p-fluorobenzyl)-5,6-dihydro-4-hydroxy-6-(p-fluorophenyl)-1-methyl-2(1H)-pyridone, or
(i) 3-(α-imino-o-fluorobenzyl)-5,6-dihydro-4-hydroxy-6-(o-fluorophenyl)-1-methyl-2-(1H)-pyridone, respectively.

The 3-α-iminobenzyl-5,6-dihydro-4-hydroxy-1-methyl-6-phenyl-2(1H)-pyridone of this example is a particularly effective minor tranquilizer and muscle relaxant agent when orally administered to an animal in need of said treatment at a dosage of 100 mg. two to four times per day.

What is claimed is:

1. A compound of the formula

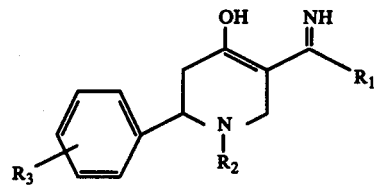

where
$R_1$ is straight chain lower alkyl or

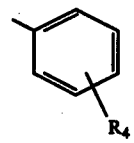

where
$R_4$ is hydrogen or halo having an atomic weight of about 19 to 36, and
$R_2$ is straight chain lower alkyl, and
$R_3$ is hydrogen or halo as defined above,
or a pharmaceutically acceptable salt thereof.

2. A compound of the formula

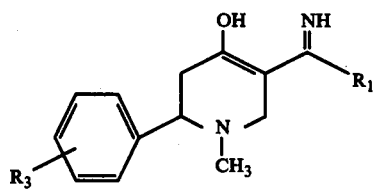

where
$R_1$ and $R_3$ are as defined in claim 1,
or a pharmaceutically acceptable salt thereof.

3. A compound of the formula

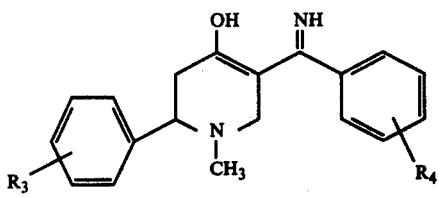

where
R$_3$ and R$_4$ are as defined in claim 1,
or a pharmaceutically acceptable salt thereof.

4. The compound of claim 1 which is 3-α-iminobenzyl-5,6-dihydro-4-hydroxy-1-methyl-6-phenyl-2(1H)-pyridone.

5. The compound of claim 1 which is 3-(α-imino-p-fluorobenzyl)-5,6-dihydro-4-hydroxy-6-phenyl-1-methyl-2(1H)-pyridone.

6. The compound of claim 1 which is 3-(α-imino-o-fluorobenzyl)-5,6-dihydro-4-hydroxy-6-phenyl-1-methyl-2(1H)-pyridone.

7. A pharmaceutical composition for use in the treatment of muscle spasms which comprises a muscle-relaxant effective amount of a compound of claim 1 and a pharmaceutically acceptable diluent or carrier therefor.

UNITED STATES PATENT AND TRADEMARK OFFICE
CERTIFICATE OF CORRECTION

PATENT NO. : 4,131,679      Page 1 of 2

DATED : Dec. 26, 1978

INVENTOR(S) : Jeffrey Nadelson

It is certified that error appears in the above-identified patent and that said Letters Patent are hereby corrected as shown below:

Col. 6, line 44, delete the phrase "isoxazole" and insert in its place the correct phrase -- isoxazolo --.

Col. 8, line 9, delete the designation "(1-H)" and insert in its place -- (1H) --.

Col. 8, claim 1, between lines 27-37, please delete the formula and insert in its place this corrected formula:

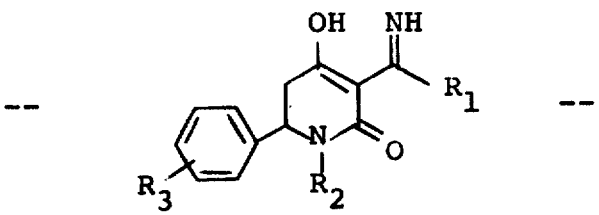

Col. 8, claim 2, between lines 55-64, please delete the formula and insert in its place this corrected formula:

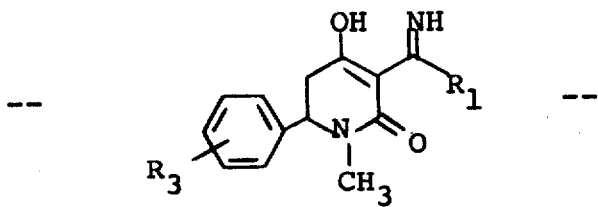

UNITED STATES PATENT AND TRADEMARK OFFICE
CERTIFICATE OF CORRECTION

PATENT NO. : 4,131,679

DATED : Dec. 26, 1978

INVENTOR(S) : Jeffrey Nadelson

It is certified that error appears in the above-identified patent and that said Letters Patent are hereby corrected as shown below:

Col. 9, between lines 1-10, please delete the present formula and insert in its place this corrected formula:

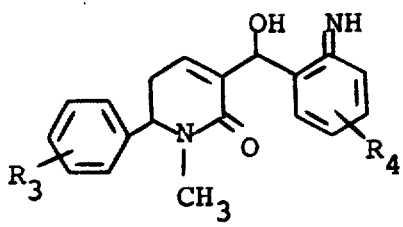

Signed and Sealed this

Nineteenth Day of June 1979

[SEAL]

Attest:

RUTH C. MASON
Attesting Officer

DONALD W. BANNER
Commissioner of Patents and Trademarks